United States Patent [19]

Kaufman et al.

[11] Patent Number: 5,250,421
[45] Date of Patent: Oct. 5, 1993

[54] METHOD FOR PRODUCING FACTOR VIII:C-TYPE PROTEINS

[75] Inventors: Randal J. Kaufman, Boston; S. Robert Adamson, Chelmsford, both of Mass.

[73] Assignee: Genetics Institute, Inc., Cambridge, Mass.

[21] Appl. No.: 824,765

[22] Filed: Jan. 17, 1992

Related U.S. Application Data

[63] Continuation of Ser. No. 260,085, Oct. 19, 1988, abandoned, which is a continuation-in-part of Ser. No. 816,031, Jan. 3, 1986, abandoned, and Ser. No. 942,338, Dec. 16, 1996, abandoned, and Ser. No. 34,882, Apr. 6, 1987, abandoned, and Ser. No. 68,865, Jul. 2, 1987, abandoned.

[51] Int. Cl.$^5$ ............ C12P 21/00; C12N 5/02
[52] U.S. Cl. .................... 435/69.6; 435/69.1; 435/172.3; 435/320.1; 435/240.2; 435/240.3; 435/240.31; 930/100; 935/33; 935/34; 935/60; 935/70
[58] Field of Search .......... 435/69.1, 69.6, 172.3, 435/320.1, 240.2, 240.21, 240.3, 240.31, 252.3, 240.1; 935/11, 34, 36, 61, 70, 71

[56] References Cited

U.S. PATENT DOCUMENTS

| | | | |
|---|---|---|---|
| 4,670,394 | 6/1987 | Pollard et al. | 435/240.21 |
| 4,740,461 | 4/1988 | Kaufman | 435/69.1 |
| 4,757,006 | 7/1988 | Toole et al. | 435/69.6 |

FOREIGN PATENT DOCUMENTS 0112174 6/1984 European Pat. Off. .
58-13389 1/1983 Japan .
0023784 2/1983 Japan .
8501961 5/1985 World Int. Prop. O. .

OTHER PUBLICATIONS

Barnes et al. 1980, Cell. 22, 649–655.
Wood et al. 1984. Nature 312, 330–337.
Weiss et al. 1977. J. Clin. Invest. 60, 390–404.
Tuddenham et al. 1984 Br. J. Haematol. 52, 259–267.
Freshney, I. R. 1983. in: *Culture of Animal Cells. A Manual of Basic Technique.* Alan R. Liss, New York. pp. 67–78.
Brinkhous et al. 1985. Proc. Natl. Acad. Sci. USA 82, 8752–8756.
Andersson et al. 1981. Biochem. J. 200, 161–167.
Lynch et al. 1985. Cell 41, 49–56.
Kruse et al. (eds.) 1973 in: *Tissue Culture: Methods and Applications.* Academic Press, New York. pp. 677–682.
Sadler et al. 1985 Proc. Natl. Acad. Sci. USA 82, 6394–6398.

Primary Examiner—Christopher S. F. Low
Attorney, Agent, or Firm—David Berstein; Thomas J. DesRosier; Bruce M. Eisen

[57] ABSTRACT

An improved method for producing Factor VIII:c-type proteins is disclosed which involves culturing mammalian cells which are capable of expressing the protein. In accordance with this invention the cells are cultured in a medium containing an effective amount of a substance comprising (a) von Willebrand Factor-type protein, (b) a phospholipid or phospholipid mixture, or a mixture of (a) and (b).

4 Claims, No Drawings

METHOD FOR PRODUCING FACTOR VIII:C-TYPE PROTEINS

This application is a continuation of application Ser. No. 07/260,085 (filed Oct. 19, 1988) now abandoned, which is a continuation-in-part of application Ser. No. 816,031 (filed Jan. 3, 1986) now abandoned, and application Ser. No. 942,338 (filed Dec. 16, 1986) now abandoned, and application Ser. No. 034,882 (filed Apr. 6, 1987) now abandoned, and application Ser. No. 068,865 (filed Jul. 2, 1987) now abandoned, the contents of each of which is hereby incorporated by reference.

BACKGROUND OF THE INVENTION

The Factor VIII complex has two distinct biologic functions: coagulant activity and a role in primary hemostasis. The analysis of Factor VIII deficiency diseases, classic hemophilia and von Willebrand's disease, have contributed to the understanding that Factor VIII is a complex of two components. The Factor VIII:c procoagulant protein (antihemophilic factor) and the Factor VIII related antigen (von Willebrand factor, VWF) are under separate genetic control, have distinct biochemical and immunologic properties, and have unique and essential physiologic functions.

The Factor VIII:c molecule is an important regulatory protein in the blood coagulation cascade. After activation by thrombin, it accelerates the rate of Factor X activation by Factor IXa, eventually leading to the formation of the fibrin clot. Deficiency of Factor VIII:c (classic hemophilia) is an X-linked chromosomal disorder that has been a major source of hemorrhagic morbidity and mortality in affected males. Treatment usually consists of frequent transfusions with blood products. The latter has resulted in a high incidence of infectious complications (such as various forms of hepatitis and acquired immunodeficiency disease) in the hemophiliac population.

The VWF molecule is an adhesive glycoprotein that plays a central role in platelet agglutination. It serves as a carrier for Factor VIII:c in plasma and facilitates platelet-vessel wall interactions. Discrete domains of VWF which bind to platelet receptor sites on glycoprotein 1b and on the glycoprotein IIb-IIIa complex, as well as binding sites on collagen have been noted. VWF is made up of multiple, probably identical, subunits each of about 230,000 daltons. VWF is synthesized in endothelial cells and megakaryocytes. In the plasma it exists as high molecular weight multimers ranging from $5 \times 10^5$ to $10^7$ daltons. Von Willebrand Factor contains 5-6% complex carbohydrate, which appears important in the molecule's ability to bind platelets. A variety of abnormalities in VWF activity can result in Von Willebrand's disease. The disorder is generally inherited in autosomal dominant fashion and may affect as many as one in 2000 individuals. Mild forms of the disease frequently go undiagnosed, whereas severely affected patients may require frequent blood product support with its associated risks.

Recently, the isolation of the genes for both Factor VIII:c and Von Willebrand Factor have made possible the production of recombinant factor VIII:c and VWF preparations, respectively, which are essentially free of contaminating viruses (Toole et al., 1984, Nature 312:342; Wood et al., 1984, Nature 312:330; Lynch et al., 1985, Cell 41:49-56; Ginsberg et al., 1985, Science 228:1401-1406). The production of Factor VIII:c or analogs thereof through recombinant DNA technology has been achieved utilizing mammalian cells transfected or transformed with appropriate expression vectors containing DNA encoding Factor VIII:c or the analogs thereof. Primary concerns for the synthesis of recombinant Factor VIII:c-type proteins include (i) the yield of recombinant protein obtainable from the culture medium, (ii) the stability of the recombinant protein so produced, (iii) the efficiency and cost of purification of the protein and (iv) the overall cost of producing purified recombinant protein.

For best results, we have heretofore typically cultured cells producing FVIII:c-type protein in media containing mammalian serum, e.g. conventional preparations of fetal bovine serum, in amounts of about 10% serum by volume relative to total media volume. (For the sake of simplicity, all serum concentrations hereinafter are expressed as a volume % of total media.) We have found that in the absence of serum supplements both the yield and stability of the recombinant FVIII:c suffer significantly. However, the cost of serum and the added inconvenience and expense in purification resulting from the addition of serum to the media rendered the use of serum an undesireable necessity and the wide scale use of recombinant FVIII:c a commercially less attractive alternative to natural FVIII:c purified from plasma. Interestingly, despite the great excitement in the medical and pharmaceutical communities over the clinical potential of recombinant FVIII:c, we are aware of no reports heretofore of the above-mentioned serum dependence, its biochemical basis or methods to circumvent it.

After extensive experimental modifications of media for FVIII:c-producing cells we have surprisingly found a method for producing higher yields of stable FVIII:c-type proteins (as described hereinafter) even when using media containing reduced amounts of serum (e.g., semi-defined media, containing ~1% serum) or essentially serum-free media (defined media). We have found that host cells producing FVIII:c-type proteins produce recoverable, stable FVIII:c-type proteins in semi-defined and defined media in yields at least comparable, and in some cases superior, to those obtained in the presence of 10% serum if the semi-defined or defined media contains a suitable amount of a hydrophobic substance such as VWF or certain phospholipids. We have further found that FVIII:c-type proteins produced in semi-defined or defined media lacking such supplements typically exhibit dramatic instability and are recoverable in extremely low yield if at all.

Evidence to date suggests either that VWF may have a stabilizing effect in vivo on the Factor VIII:c in plasma, or that the VWF can ellicit the in vivo release from storage depots or stimulate the in vivo synthesis and/or secretion of Factor VIII:c (Weiss, H. J. et al., 1977, J. Clin. Invest. 60: 390-404). It has also been suggested that thrombin-activated Factor VIII (derived from natural, human FVIII) is stabilized by phospholipids, presumably with respect to thrombin-mediated degradation. See Andersson and Brown, 1981, Biochem. J. 200:161-167. However, to our knowledge there is no suggestion in the prior art as to any possible effect(s) of VWF or phospholipid on the in vitro production of Factor VIII:c-type proteins (where, for example, thrombin is substantially absent) or any suggestion of media supplements for the production of Factor VIII:c comprising VWF or a VWF-type protein and/or phospholipids either substantially free from the complex mixture of components present in mammalian serum or in concentrations higher than afforded by 10% serum supplements in accordance with this invention. It should be noted that mammalian serum contains VWF. As a point of reference, conventional media for mammalian cells which contains about 10% serum, contains about 1ug VWF/ml media.

SUMMARY OF THE INVENTION

This invention concerns an improved method for the production of Factor VIII:c-type proteins.

"Factor VIII:c-type" proteins, as the term is used herein, means proteins exhibiting Factor VIII:c-type procoagulant activity. Factor VIII:c-type proteins within the ambit of this invention are encoded for by DNA sequences capable of hybridizing to DNA encoding Factor VIII:c under conditions that avoid hybridization to non-Factor VIII:c genes, e.g., under conditions equivalent to 65° C. in 5×SSC (1×SSC=150 mM NaCl/0.15M Na citrate). In addition to natural mammalian, e.g. human, Factor VIII:c, Factor VIII:c-type proteins include, for example, proteins which contain deletions of one or more amino acids between the 90 Kd and 69 Kd cleavage sites with respect to native Factor VIII:c, as described in greater detail in International Application No. PCT/US86/00774, published 23 October 1986. Factor VIII:c-type proteins also include Factor VIII:c analogs containing deletion(s) of one or more amino acids between the 50/40 cleavage site and the 69 Kd cleavage site which may be produced by methods analogous to those disclosed in PCT/US86/00774. Factor VIII:c-type proteins further include analogs (with or without deletions as mentioned above) wherein one or more of the cleavage sites spanning arginine residues at positions 226, 336, 562, 740, 776, 1313, 1648 or 1721 have been rendered resistant to proteolytic cleavage, e.g., by replacement of one or more amino acids with different amino acids by conventional site-directed mutagenesis of the cDNA to be expressed. Factor VIII:c-type proteins thus include natural Factor VIII:c, "recombinant" Factor VIII:c and analogs thereof having procoagulant activity, and non-recombinant Factor VIII:c or analogs thereof produced by cell lines derived from cells which produce the protein.

The method of this invention thus utilizes mammalian cells which contain DNA encoding a Factor VIII:c-type protein and which are capable of expressing the protein. In accordance with the method of this invention the cells are cultured in media containing an effective amount of a stabilizing substance for a Factor VIII:c-type protein. Such substances include: (i) a VWF-type protein; (ii) a stabilizing phospholipid or phospholipid mixture; and (iii) mixtures containing a VWF-type protein and phospholipid(s). Although termed "stabilizing substances", it should be understood that VWF-type proteins may possess, in addition to a stabilizing effect on Factor VIII:c-type proteins, other effects which result in higher levels of synthesis and/or export of the Factor VIII:c-type proteins from the producing cells. VWF-type proteins include truncated or otherwise modified analogs of von Willebrand Factor which are encoded by a cDNA capable of hybridizing under to a cDNA encoding a mammalian VWF under hybridization conditions such as those mentioned above, and which retain the ability to stabilize Factor VIII:c-type proteins or otherwise result in increased production and/or accumulation of the FVIII-type proteins in the culture media.

For example, truncated forms of human VWF which may be used in the practice of this invention include (i) Δpro VWF, which lacks the "pro" sequence of VWF; (ii) Δmature VWF, which comprises the "pro" sequence without the mature sequence; and, (iii) VWF-5'-Sac, which comprises the sequence of pro-VWF from the N-terminus to the 5' Sac I restriction site and includes the "pro" portion of VWF as well as the first "D" domain of the mature sequence A full-length peptide sequence, nucleotide sequence and restriction map for VWF have been published. See, e.g. International Patent application Publication No. WO 86/06096 (Appln. No. PCT/US86/00760). With reference to that sequence, the "pro" portion spans amino acid positions 23 through Arg-763 and the "mature" protein spans amino acid positions 764 through 2813. A cDNA encoding Δpro VWF may be prepared by conventional loop-out mutagenesis using, for example, the full-length VWF cDNA present in the vectors described hereinafter and a synthetic loop-out oligonucleotide complementary to part or all of the VWF "pre" sequence and mature sequence but lacking the codons complementary to the "pro" sequence. A cDNA encoding Δmature VWF may be prepared by analogous methods or by making use of convenient restriction sites in the full length VWF cDNA to remove part or all of the mature sequence. Where only part of the mature sequence is thus removed, remaining cDNA regions encoding mature peptide sequence may be excised by conventional loop-out mutagenesis. Alternatively, Δmature VWF and VWF-5'-Sac may be produced by conventional mammalian expression of VWF cDNAs which have been mutagenized by conventional oligonucleotide-directed mutagenesis to insert a translational stop codon immediately 3' to the peptide sequence one wishes to produce. Other truncated or otherwise modified forms of VWF may also be prepared by analogous methods and may also be useful in the practice of this invention as may be readily determined by methods disclosed hereinafter (see e.g. the Examples which follow). In particular, it is contemplated that other truncated forms of VWF which contain one or more of the "D" domains (of which two are present in the "pro" portion) may also be useful in the practice of this invention. At present, Δpro VWF is preferred among truncated variants of VWF for use in accordance with this invention.

Potential advantages of the use of these and similar truncated or otherwise modified forms of VWF include (i) imposing less stress on the producing cells by directing the synthesis, post-translational modification and export of significantly smaller proteins; (ii) decreased viscosity of the conditioned media due to the presence of smaller VWF-type proteins and the absence of higher molecular weight VWF-type multimers; and (iii) more facile purification of the FVIII-type protein from the truncated VWF-type protein rather than from the full-length VWF protein.

VWF-type proteins may be readily produced and characterized, e.g. by conventional expression, preferably in mammalian cells, of cDNAs encoding the VWF-type protein. Such VWF-type proteins may then be tested for efficacy in the production of FVIII-type proteins by the methods described hereinafter, eg, in the Examples which follow. The cDNA may have been produced by mutagenesis in a random or site-specific manner. Mammalian VWF as well as VWF-type proteins are referred to herein simply as "VWF".

One embodiment of this invention encompasses an improved method for producing Factor VIII-type proteins which comprises culturing mammalian cells capable of producing a Factor VIII-type protein in a medium to which exogenous VWF-type protein has been added. Exogenous VWF-type protein may thus be added to the medium, as is described in greater detail hereinafter, e.g., by virtue of prior conditioning of the medium by cells producing VWF-type protein, by coculturing cells producing VWF-type protein with cells producing a Factor VIII-type protein, by using cells genetically engineered to produce both VWF-type protein and a Factor VIII-type protein, or by adding exogenous VWF-type protein obtained, e.g. from conditioned medium.

Preferred effective amounts of VWF-type protein generally range from about 0.1–10 ug VWF/ml media, with ~1–~3 ug/ml being more preferred and ~2-18 3 ug/ml being especially preferred. It should be noted, however, that in cases where the exogenous VWF-type protein is added to the medium by using cells genetically engineered to produce both VWF-type protein and a Factor VIII-type protein, amounts at the lower end of the general range may be preferred. Lower media concentrations of the VWF-type protein may be useful in such methods since greater effective concentrations of the exogenous VWF-type protein may be available at the site of production and secretion into the medium of the Factor VIII-type protein despite the lower media concentration. Furthermore, the use of cells which produce both proteins is presently preferred to the co-culturing of different cells which individually produce one or the other protein. This is so because the latter method may introduce potential complications to the cell culture process such as variable growth rates of the different cells, and inherently results in a lower density for cells producing the FVIII-type protein (by virtue of the presence of the cells producing the VWF-type protein).

One readily obtainable source of suitable phospholipids comprises commercially available dry milk preparations such as dried skim milk and low-fat skim milk. Such dried milk preparations may be added to the media in amounts ranging from about 0.01%–10% (weight of dry milk/volume of media). For optimal effect on Factor VIII production with minimal toxic effect on the cells, about 1%–3% dry milk is presently preferred. The dry milk preparations may be conveniently sterilized by first preparing a 10% aqueous suspension of the milk and autoclaving. Another readily obtainable source of suitable phospholipids is commercially available soybean lecithin, which may be added to the medium in accordance with this invention, preferably in liposome form.

"Phospholipid" as the term is used herein means an ester of phosphoric acid containing one or two molecules of fatty acid, an alcohol and a nitrogenous base. Examples of such phospholipids include Cephalin, phosphatidyl serine: phosphatidyl choline mixtures, phosphatidyl inositol, phosphatidyl ethanolamine, soybean lecithin and mixtures thereof, with soybean lecithin being especially preferred. Other phospholipids useful in this method as well as effective and/or optimal concentrations and/or mixtures thereof may be readily identified by those skilled in the art using methods described in greater detail hereinafter. Presently preferred effective amounts of phospholipid or phospholipid mixtures comprise about 1–1000 ug phospholipid or phospholipid mixture per ml of culture media, with concentrations greater than about 100 ug/ml being more preferred and concentrations between about 200–300 ug/ml being especially preferred. The utility of such phospholipid supplements is certainly surprising in view of the toxicity we have observed of such compositions on mammalian cells such as CHO cells. Indeed, when using phospholipid supplements in accordance with this invention, it is preferable to additionally include bovine serum albumin (BSA) in the medium to protect the cells from such toxicity. Suitable concentrations of BSA range from about 1 to about 10g BSA/l medium, depending on such factors as the amount of phospholipid used, the hardiness of the cells, and the degree of toxicity observed in the absence of BSA. Additionally, it is presently preferred to add the phospholipid mixture to the culture media in the form of liposomes, preferably having a diameter of up to about 500 nm. Preferably the liposomes are unilamellar, although multilamellar liposomes may also be used. Most preferably the diameter of the liposomes is less than about 100 nm. Furthermore, liposomes made by conventional methods from said phospholipids may be used, either in admixture with or containing the Factor VIII:c-type protein, as a carrier or vehicle for administering the protein to patients. Where dried milk is used as the source of phospholipids, the dried milk may be added directly (rather than in the form of liposomes) to the media.

In one embodiment, cells producing VWF-type protein, such as cells suitably engineered to produce the VWF-type protein, are cultured in the medium to condition it with the VWF-type protein either prior to or simultaneously with the culturing of cells which produce a Factor VIII:c-type protein. Alternatively the recombinant VWF-type protein may be separately produced and added as an exogenous supplement to the media to be used for culturing the cells producing the Factor VIII:c-type protein. In another embodiment the cells which produce Factor VIII:c-type protein are suitably engineered, i.e. effectively transformed with transcription unit capable of directing the production of the VWF-type protein, such that the VWF-type protein and the Factor VIII:c-type protein are co-expressed by the same cells. In a further embodiment of this invention the media used for culturing the cells producing the Factor VIII:c-type protein contains both VWF-type protein, by virtue of one of the above-mentioned processes, and stabilizing phospholipid(s). In that case, it may be desirable to use reduced amounts of each component relative to the amounts used if used alone. By using appropriately supplemented defined media in accordance with this invention high levels of recoverable, stable Factor VIII:c-type activity are produced which may then be recovered and purified without the necessity for separation of serum components therefrom. The culture media used in this invention may additionally contain mammalian-derived serum, e.g. fetal bovine serum, preferably in amounts less than about 10%, more preferably in amounts less than about 5%, and even more preferably in amounts between 0 and 1%, although essentially serum-free media is especially preferred. Other conventional mammalian cell culture media supplements may also be added.

It should be noted that in the practice of this invention, the FVIII-type protein so produced may be conveniently recovered from the culture medium into which it is secreted, and further purified, if desired, by any of a number of conventional procedures, including e.g.

conventional chromatographic methods and immunoaffinity-based methods.

This invention is illustrated in the following examples which set forth typical procedures demonstrating, among other things, the ability to overcome "serum" dependence in the production of recoverable, active Factor VIII:c-type proteins by using phospholipids, and/or VWF-type protein as media supplements. The examples are set forth to aid in an understanding of the invention but are not intended to, and should not be construed to, limit in any way the invention as set forth in the claims which follow thereafter.

EXAMPLE I

Establishment of Chinese Hamster Ovary Cell Lines which Express Human Factor VIII:c The Factor VIII:c expression plasmid used in this Example was RxPy VIII-I which contains in clockwise order the polyomavirus enhancer, the first leader sequence of the adenovirus tripartite leader sequence, a Factor VIII:c transcription unit followed by a DHFR gene and SV40 polyadenylation signal, and a gene encoding tetracycline resistance. This plasmid was introduced into dihydrofolate reductase (DHFR) deficient Chinese hamster ovary cells by cotransformation with a DHFR expression plasmid and subsequent selection for cells that grow in the absence of added nucleotides. One particular pool of transformants designated lig 1 was subsequently grown in increasing concentrations of methotrexate (MTX) in order to amplify the DHFR and Factor VIII genes. The resultant cell line expressed high levels of Factor VIII activity as determined by either the ability to clot Factor VIII deficient plasma [Clotech (APPT) assay] or by the ability to generate Factor Xa in the presence of Factor IXa, phospholipid, calcium, and Factor X (Kabi Cotest assay). The ability of these CHO cells to produce Factor VIII:c is shown in Table I. The Factor VIII activity increased 10,000 fold with increasing levels of MTX resistance which correlated with the Factor VIII gene copy number. Other expression vectors may also be used in place of RxPy VIII-I so long as they are capable of directing the expression of Factor VIII:c or analogs thereof. Such vectors include, for example, pCVSVL2-VIII (ATCC No. 39813, see European Application No. 85202121.1) and pDGR-2 (ATCC No. 53100, see PCT/US86/00774-deletion analog). Other Factor VIII:c expression vectors containing, for example, the SalI fragment from pCVSVL2-VIII or pSP64-VIII (ATCC No. 39812) may be prepared using conventional expression vectors and techniques. The SalI fragment from either vector contains a DNA sequence encoding full-length Factor VIII:c.

TABLE I

Factor VIII Expression in Transfected and Amplified CHO cells

| Pool | MTX (uM) | mU/ml/day of VIII:c |
|---|---|---|
| Lig 1 | 0.0 | 0.1 |
| | 0.02 | 11.5 |
| | 0.1 | 88.0 |
| | 1.0 | 288, 545* |
| | 5.0 | 644, 875* |
| | 20.0 | 1075 |

*Represents samples from two independent assays

Plasmids pAdD26SVpA(3) (Kaufman and Sharp, 1982, Mol. Cell. Biol.) and plasmid pRXPy-VIII-I were digested with Cla 1 and the resultant linearized DNA was ligated in vitro and coprecipitated with CaPO4 and used to transfect CHO DHFR deficient DUKX-BII cells. Cells which efficiently expressed DHFR would be expected to contain the enhancer element from pRXPyVIII-I associated with the DHFR gene from pAdD26SVpA(3). Results have been consistent with this hypothesis. Subsequent selection for increased DHFR expression by propagation of the cells in increasing concentrations of MTX results in cells which have amplified the Factor VIII gene and the DHFR gene. At each level of MTX selection, samples of the conditioned media (approximately $10^6$ cells/ml in alpha media supplemented with 10% fetal bovine serum) were taken for Factor VIII:c activity assay determined by the Kabi Coatest method modified to obtain sensitivity better than 0.05 mU/ml. Comparable results were also obtained by the one-stage activated partial thromboplastin time (APTT) coagulation assay using Factor VIII:c deficient plasma. All samples exhibited thrombin activation of 30-50 fold. For thrombin activation the samples were pretreated 1-10 min with 0.2 units/ml thrombin at room temperature.

EXAMPLE II

Serum Dependence of Factor VIII:c Synthesis

A subclone of the lig 1 CHO cells of Example I (Lig 1 2 A C subclone B10 in 0.1 uM MTX at 80% confluence) which are rinsed and fed with media containing 10% FCS or defined media (serum free, containing: 5 mg/ml BSA, insulin, transferrin, selenium, hydrocortisone and putrescine) accumulate Factor VIII activity. The rate of appearance in defined media is roughly 4-fold lower than in serum-containing media The 4-fold difference becomes larger as the cells are propagated in the absence of serum. This results from inefficient rinsing of the cells. The rate of Factor VIII:c appearance increases fairly linearly up to 24 hrs. which suggests the VIII is stable in the media. This result is similar to results obtained with COS cells at lower levels of VIII expression (Approx. 10 mU/ml/day). Cephalin, a mixture of phospholipids, can counteract at least part of the serum deficiency. A subclone of the CHO cells of Example I (Lig. 2 A pool in 20 uM MTX) were separately cultured with and without serum and rinsed after 4 hr. The two CHO cultures were then split again, and a portion of the serum+ and of the serum− CHO cells were supplemented with 5 uM cephalin for an additional 2 hr. The other portion of the serum+ and serum− CHO cells were not supplemented with cephalin. Media was assayed at 6 hrs. and 25 hrs. and results shown below:

| Conditions | | FVIII:c Activity* | |
|---|---|---|---|
| Serum | Cephalin | 6 hr. | 25 hr. |
| +FCS | +Ceph | 594 | 1044 |
| −FCS | +Ceph | 408 | 514 |
| +FCS | −Ceph | 563 | 1492 |
| −FCS | −Ceph | 140 | 372 |

The results suggest that cephalin alone can increase VIII activity in the absence of serum but that its effect is short lived (i.e. observed after 2 hrs. but is diminished at 25 hrs.). In one experiment the concentration of cephalin was increased and there was no further increase in VIII activity. This indicated some component in the cephalin was not rate limiting.

Part of the cephalin effect can be elicited by a simpler mixture of phospholipids or by single phospholipids. Cells (a subclone of the CHO cells of Example I, Lig 1 2 A 0.02 pool in 20 uM MTX) were fed with 10% fetal calf serum or serum free media for 24 hrs. and then either cephalin (5um) or a mixture (1:4) of phosphatidyl serine and phosphatidyl choline (PCPS) were added to serum free cultures. Results from media assayed after 2 hrs. were:

| conditions | FVIII:c Activity |
|---|---|
| Serum Free | 100 |
| Serum Free + Cephalin | 489 |
| Serum Free + PCPS | 230 |
| 10% FCS | 613 |

This result demonstrates that phospholipids alone can increase VIII activity in conditioned media.

Analysis of the thrombin activation of VIII expressed in CHO cells growing under different conditions suggests that the presence of serum decreases the degree of thrombin activation. CHO cells (Lig 1 2 A pool in 20 uM MTX) were rinsed and fed with media containing 10% fetal calf serum or defined media (5 mg/ml BSA, transferrin, selenium, insulin, hydrocortisone, putrescine). 24 hrs. later either cephalin or 10% FCS was added and 2 hrs. later samples taken for assay and measure of thrombin activatibility:

| Sample Media | Added at 24 h | Assay at 26 hrs. Cobas mU/ml | mU/ml | Coagulation Assay (fold activation) |
|---|---|---|---|---|
| Defined media | — | 315 | 300 | 20X |
| Defined media | 5 uM cephalin | 752 | 1040 | 34X |
| Defined media | 10% FCS | 684 | 440 | 8.4X |
| + 10% FCS | — | 1078 | 1200 | 10X |
| + 10% FCS | 5 uM cephalin | 1154 | 1120 | 14X |
| Defined media | 10% boiled FCS | 543 | — | — |

These results suggest that the presence of serum increases the activity produced compared to serum free media but reduces the thrombin activatibility. In contrast, cephalin may compensate for the serum effect on increasing the activity of the VIII produced but does not reduce the thrombin activatibility. Thus, in serum free media, with the addition of cephalin 2 hrs. prior to harvest, CHO cells produce VIII at 1 unit/ml and this material exhibits a 34 fold thrombin activation. This experiment also demonstrates that 10% FCS added to serum free media 2 hrs. prior to assay can also increase the amounts of VIII activity. This ability was not diminished by boiling the serum 10 min prior to its addition. Thus, the serum factor required for VIII activity is heat stable. We conclude that the serum factor required for increasing VIII may comprise two components: a phospholipid and another, heat stable factor which may be required to stabilize the phospholipid.

To determine whether the 10% serum was limiting for Factor VIII:c expression in the highly amplified CHO cell lines, we monitored the effect of increasing amounts of serum on the ability to elicit factor VIII:c activity in the cell line 10A1. 10A1 is a clone derived from selection of the Lig 1 pool for growth in 1 mM MTX. This experiment demonstrated the effect on Factor VIII activity of adding increasing amounts of fetal bovine serum to the 10A1 cells for 24 hrs. 50% serum yielded three-fold more activity in the 24 hr. conditioned media compared to 10% serum. Other results have indicated that the amount of active Factor VIII antigen is correspondingly increased when cells are propagated in 50% serum. Other cell lines, which express slightly lower levels of Factor VIII:c show less dramatic increases in Factor VIII:c activity upon growth in higher concentrations of serum. Thus there appears to be some limiting requirement for Factor VIII: expression in higher producing cells such as those which would be desirable for commercial-scale production of Factor VIII.

Example III

Serum Dependence of rFactorVIII:cSynthesis in Suspension Cultures of CHO

The following table illustrates the dependency of recombinant Factor VIII:c (rFVIII) activity on serum levels in culture. A relatively low rFVIII producer, clone 1E6, was grown in suspension culture for 3 to 4 days in medium containing various concentrations of fetal bovine serum (FBS).

| Serum Concentration in Medium* | rVIII Activity (mU/ml) after 3-4 days | Average Productivity (U/$10^6$ cells/day) |
|---|---|---|
| 10% FBS | 318 | 0.19 |
| 5% FBS | 100 | 0.03 |
| Defined* | 4 | ¼-0.01 |

*RPMI 1640 was employed as basal medium for all of the above. The defined medium consists of insulin, 5 ug/l; transferrin, 5 ug/ml; selenium, 5 ng/ml; hydrocortisone, $10^{-8}$ M, putrescene, 100 ng/ml; BSA, 5 mg/ml.

The same serum dependence has been observed with other rFVIII secreting CHO cell lines. These results do not reflect genetic instability since original expression levels can be regained on addition of serum.

We have found that addition of phospholipid to culture medium can replace the serum requirement, however relatively high concentrations of phospholipid are required (on the order of 10–20 fold higher than previously used with serum-containing media). With respect to the dependence of the recovery of FVIII activity on phospholipid concentration, we have found that supplementing defined media (DM) with 240 ug soybean lecithin (SL)/ml media yielded (after 24 hrs) about twice as much FVIII activity as was obtained in DM containing 160 ug SL/ml and five times as much FVIII activity as was obtained in DM containing 80 ug SL/ml. Nonetheless, DM containing 80 ug SL/ml provided measurably more FVIII activity than DM containing 1% Fetal Bovine Serum(FBS)(semi-defined media), while the semi-defined media provided significantly more FVIII activity than did DM alone. Significantly, the level of rFVIII generated over a 24h period in defined medium in the presence of 240 ug SL/ml media is at least as high as that generated in DM supplemented with 10% FBS. Increasing the concentration of SL above 240ug/ml resulted in no further increase in rVIII activity in this experiment. Illustrative results of one experiment are shown below:

| Media | rFVIII activity after 24 h |
|---|---|
| Defined Media (DM) | ~40 mU/ml |
| DM + Soybean lecithin (SL) | ~270 mU/ml |

| Media | rFVIII activity after 24 h |
|---|---|
| (240 ug SL/ml media) Media containing Fetal bovine serum (FBS) (10% FBS) | ~200 mU/ml |

This data illustrates the increase in the rFVIII:c activity obtained with relatively high concentrations (e.g., 240 ug/ml) of soybean lecithin phospholipid in the absence of fetal bovine serum. CHO cells (1E6 in 0.1 umolar MTX) were suspended at a concentration of $3 \times 10^5$ cells/ml in defined medium containing 5 g/1 of bovine serum albumin either in the absence or presence of phospholipid or medium containing 10% FBS for 24 h at 37° C. At the conclusion of the incubation samples of cell-free conditioned medium were assayed for rFVIII:c activity by a chromogenic assay.

We have found that the addition of phospholipid in amounts up to about 320 ug/ml media causes no marked changed in cell growth in either defined or semi-defined media. In one set of experiments we found that maximum rFVIII activity was obtained in the culture where 320 ug phospholipid/mL media was added. In semi-defined medium, maximum levels were obtained after 72 h where 240 ug/mL of soybean lecithin was added. These and other data illustrate that soybean lecithin added stepwise to cultures on days 0, 1, 2 and 3 allowed production of rFVIII. The optimum concentrations were around 240 ug/mL in these and other experiments regardless of the method of preparation of the phospholipid.

The cellular productivities in two different CHO cell lines from experiments similar to the above are shown below.

| Medium | Average Productivity (u/10⁶ cells/day) | (Cell Line - 1E6) |
|---|---|---|
| 10% FBS | 0.19 | |
| 5% FBS | 0.03 | |
| Defined | ¼-0.01 | |
| Defined + SL | 0.24 | |
| Defined + 1% FBS + SL | 0.25 | |

| Medium | Average Productivity* | (Cell Line - H9.05) |
|---|---|---|
| 10% FBS | 0.43 | |
| Defined +1% FBS + SL | 0.51 | |

*Units as above

Thus, productivities of rFVIII from rCHO cells are at least equivalent in defined medium supplemented with phospholipid as in serum-containing medium. However, as illustrated by the data above, the bulk quantity of rFVIII produced in defined medium is less than in serum containing medium. This is due to the fact that cells grow more rapidly and to higher cell densities in serum-containing medium (rather than being more productive). On supplementation of defined medium with small quantities of serum (e.g. 1%) cell growth is improved. Indeed, after a short period of adaption cells will grow almost as well in semi-defined medium as in 10% FBS supplemented medium. We have found that rCHO cell lines (e.g., our H9.05) grow to similar cell densities and are at least equally productive (in Factor VIII) in phospholipid supplemented semi-defined medium as in 10% FBS supplemented medium.

Furthermore, we have also examined the physical nature of the soybean lecithin preparations. A size profile of a typical phospholipid preparation, where the soybean lecithin is suspended in saline and passed three times through a Manton-Gaulin homogenizer, then filtered through a 0.2 um filter was obtained. The average mean size of the liposomes was around 100nm in diameter, suggesting that the majority of liposomes resulting from this process are small unilamellar vesicles (SUV's). The following experiment indicates that the size of the soybean lecithin liposomes may play an important role in the efficacy of the phospholipid, i.e., the ability of the SL to cause an increase in FVIII:c expression.

A soybean lecithin preparation was constituted in saline but not homogenized. The preparation contained significantly less SUV's than a normal (i.e., with homogenization) preparation (only 44% of the liposomes were below 100nms vs 74% in a normal prep). It also contained a significant population of multilamellar vesicles (MV's) which were around 500 nm's in diameter (30-40% of the total liposomes were MV's) which are present in only small quantities (usually <5%) in normal preparations. The efficacy of this sample was reduced to about 60% of a normal sample indicating that the size of the liposomes may play an important role in the efficacy of the phospholipid.

EXAMPLE IV

Porcine VWF can act to elicit Factor VIII:c activity from CHO cell propagated in the absence of serum Lig 1 (20 uM MTX) cells obtained as in Example I were rinsed and fed defined media (alpha media containing insulin, transferrin, selenium, hydrocortisone, and putrescine, glutamine, and penicillin and streptomycin) added back with increasing concentrations of bovine serum albumin or with similar concentrations of ovalbumin Table II. Both proteins can act to elicit Factor VIII:c expression. However, when partially purified VWF is added back to media containing 5 g/1 bovine serum albumin, the Factor VIII:c activity increased four-fold to even greater than the levels obtained upon propagation of the cells in 10% fetal bovine serum. This dramatically demonstrates the ability of VWF to elicit Factor VIII:c activity in the absence of serum. This result has been duplicated with different preparations of porcine VWF and also with purified human VWF.

In order to demonstrate that the ability to elicit factor VIII:c was due to VWF, the following experiment was performed. Cells which express Factor VIII:c were incubated in the presence of media containing serum derived from human VWF deficient plasma. Factor VIII:c activity in the CHO Lig 1 cells incubated in VWF deficient serum was 25% the level compared to normal human serum. When the porcine VWF preparation was added back to the VWF deficient serum, the Factor VIII activity increased to the 10% fetal bovine serum value. The effect could be elicited with as little as 2.50 ug/ml of VWF. See Table IIA. In another experiment, when the VWF concentration was decreased to 0.25 ug/ml, the activity was only 50% that of the 10% fetal bovine serum level.

The CHO cell line 1E6 which had been adapted over a 2-3 month period to grow in the absence of serum, in defined medium, was used in the following experiment in order to demonstrate that exogenous VWF could increase the level of rVIII expression in defined medium in the absence of even residual amounts of bovine VWF. The data presented below shows that supplementation of defined medium with approximately 1 microgram/mL of porcine VWF allows expression of rFVIII equivalent to the level obtained in 10% fetal bovine serum supplemented medium. Since these cells had been grown for more than 3 months in the absence of FBS no trace bovine VWF was present. Thus the observed increase in rFVIII:c levels was likely due to exogeneous VWF.

| Effect of VWF on rFVIII Expression in the Absence of Serum | |
|---|---|
| MEDIA | rFVIII (mU/ml) |
| Defined Media (DM) | ~40 |
| DM + VWF | ~190 |
| Media containing FBS (10%) | ~200 |

This data illustrates the increase in the rFVIII activity by exogenous, partially purified VWF (porcine) in the absence of fetal bovine serum. CHO cells (1E6 in 0.1 micromolar MTX) were suspended at a concentration of 3×10E5 cells/mL in defined medium containing 5 g/L of bovine serum albumin either in the absence or presence of partially purified procine VWF (at approximately 1 microgram/mL) or medium containing 10% FBS for 24 h at 37° C. At the conclusion of the incubation samples of cell-free conditioned medium were assayed for rFVIII:c activity by chromagenic assay.

TABLE II

| Factor VIII:c Expression in Defined Media with VWF Added back to Lig 1 Cells | |
|---|---|
| Defined Media + | Units/ml/day |
| Ovalbumin (g/l) | |
| 0 | 0.164 |
| 0.5 | 0.189 |
| 1.0 | 0.215 |
| 2.0 | 0.280 |
| 5.0 | 0.290 |
| 20.0 | 0.380 |
| 5.0 with procine VWF at 2.5 ug/ml | 1.200 |
| Bovine Serum Albumin (g/l) | |
| 0 | 0.190 |
| 0.5 | 0.320 |
| 1.0 | 0.380 |
| 2.0 | 0.375 |
| 5.0 | 0.530 |
| 20.0 | 0.490 |
| 5.0 with porcine VWF at 2.5 ug/ml | 1.350 |
| 10% Fetal Bovine Serum | 0.978, 1.075 |

TABLE IIA

| Effect of VWF on Factor VIII Production | |
|---|---|
| MEDIA | Mu/ml/day |
| 10% fetal bovine serum | 1321 |
| defined media with 5 g/l bovine serum albumin | 342 |
| 10% normal human serum | 937 |
| 10% VWF deficient human serum | 246 |
| 10% VWF deficient human serum with porcine VWF added back at: | |
| 2.5 ug/ml | 1124 |
| 20 ug/ml | 1397 |

In order to examine the effect of added VWF on the amount of Factor VIII:c in the conditioned media, cells were labeled with a 1 hr. pulse of 35—S methionine and chased in either media containing 10% fetal bovine serum, 10% VWF deficient human serum, or 10% VWF deficient human serum with porcine VWF added back. Results demonstrated that upon addition of VWF to VWF deficient serum, more Factor VIII:c (both the heavy 200 kDa and the light 76 kDa chains) was present in the media. No change in the intracellular synthesis of Factor VIII:c was observed. VWF addition to 10% fetal bovine serum resulted in no change in the level of Factor VIII:c in the conditioned media. These experiments indicate the VWF is necessary for the secretion and/or stability of Factor VIII:c.

EXAMPLE V

Expression of Human VWF in COS Cells

The cloning of a partial segment of the human VWF cDNA has previously been reported (Ginsberg, et al. 1985, Science). Subsequent to that report, the full length VWF cDNA has been assembled and its sequence determined. The cloning, sequence and expression of VWF have been described in detail in International Application No. PCT/US86/00760, published on 23 October 1986. We have inserted the full length cDNA clone into the expression vector pMT2 to produce pMT2-VWF (ATCC No. 67122). pMT2-VWF contains the adenovirus associated (VA) genes, SV40 origin of replication including the transcriptional enhancer, the adenovirus major late promoter including the adenovirus tripartite leader and a 5' splice site, a 3' splice site derived from an immunoglobulin gene, the VWF coding region, a non-coding DHFR insert, the SV40 early polyadenylation site, and the pBR322 sequences needed for propagation in *E. coli*. Details of this vector, which is a derivative of pQ2, are provided in Kaufman, Proc. Natl. Acad. Sci., USA 82:689–693 (1985). pMT2-VWF DNA was then prepared for COS cell transfection by conventional methods. Sixty hours after DEAE dextran mediated transfection of COS cells, the cells were labelled with 35-S methionine and media and cell extracts were immunoprecipitated with a rabbit anti-human polyclonal antibody (Calbiochem) and precipitates analyzed by SDS reducing gel electrophoresis. Our results demonstrated a significant amount of VWF is synthesized in the transfected COS cells, the majority of its being secreted. In the conditioned media there is an approximately 260 kDa protein and a 220 kDa protein which resembles the completely processed form of VWF. Approximately 50% of the VWF synthesized is processed to the 200 kDa form. When analyzed for multimer formation by non-reducing gel electrophoresis, it was found the VWF was associated into multimers, but not of extremely high molecular weight like those seen in plasma. The multimers ranged up to 1 million daltons by a rough estimate. Analysis of the VWF antigen in the COS cell conditioned media indicated the presence of human VWF at 0.35 ug/ml. Other analyses have indicated that the VWF expressed in COS cells specifically binds both platelets and collagen.

EXAMPLE VI

Recombinant VWF can elicit the expression of human Factor VIII:c

The VWF expression plasmid pMT2-VWF was transfected onto COS cells by DEAE dextran mediated transfection and 36 hours post-transfection, the media changed to serum free (DMEM lacking serum). 72 hours later the COS cell conditioned media was harvested and applied to the CHO Lig 1 cells (20 uM MTX resistant) which were previously rinsed with serum-free media (at $10^6$ cells/ml). Twenty-four hours later the media was taken from the CHO cells and assayed for Factor VIII activity. The results are shown below and compared to Factor VIII:c activities from CHO cells propagated in 10% fetal bovine serum and in serum-free media for 24 hours. These results demonstrate the ability of rVWF to elicit Factor VIII from CHO cells.

| Media on CHO Lig 1 (20 uM MTX) | mU/ml Factor VIII:c |
|---|---|
| Conditioned media from mock transfected COS cells | 141 |
| Conditioned media from VWF transfected COS cells* | 423 |
| 10% Fetal Bovine Serum | 950 |
| Serum-free media | 30 |

*The conditioned media in this experiment contained 0.3 ug/ml of human VWF.

EXAMPLE VII

Introduction, Expression, and Amplification of VWF Genes in CHO Cells which express Factor VIII:c For expression of VWF in Chinese hamster ovary (CHO) cells, a second expression vector, pMT2ADA-VWF (ATCC #67172), was used with a protocol of selection for cells over-expressing the enzyme adenosine deaminase to amplify the plasmid sequences (Kaufman et al., 1986, Proc. Natl. Acad. Sci. 83:3136; U.S. Ser. No. 619,801). A factor VIII:c expressing cell line which was cloned from ligl 2-a (from example I) in 1 mM MTX and designated 10A1, was used as recipient for transfer of pMT2ADA-VWF. pMT2ADA-VWF was introduced into 10 A1 cells by protoplast fusion as described (Sandri-Goldin et al., 1981, Mol. Cell. Biol. 1:743). *E. coli* DH5 cells harboring pMT2ADA-VWF (DH5 was used to minimize homologous recombination and deletion of the VWF sequences) were grown in 50 ml of L-broth containing 50 ug/ml ampicillin to an $A_{600}$ of 0.6. Chloramphenicol was added to 250 ug/ml and the culture incubated at 37° C. for an additional 16 hrs, in order to amplify the plasmid copy number. A suspension of protoplasts was prepared as described (Sandri-Goldin et al., 1981), added to 10A1 cells at a ratio of approximately $1-2 \times 10^4$ protoplasts/cell, and centrifuged onto the cells at 2000 rpm for 8 minutes in an IEC model K centrifuge. After centrifugation, the supernatant was removed by aspiration and 2 ml of polyethylene glycol solution (50g of PEG 1450, Baker Chem. Co., in 50 ml of Dulbecco's modified medium) was added to each plate. Cells were centrifuged again at 2000 rpm for 90 seconds, the polyethylene glycol solution removed, and the plates rinsed 3 times in alpha medium containing 10% (v/v) fetal calf serum. Cells were then plated into tissue culture dishes in medium containing 100 ug/ml kanamycin, 10 ug/ml each of penicillin and streptomycin, and 20 uM MTX. Two days later the cells were trpysinized and subcultured 1:15 into ADA selective media with 10% dialyzed fetal calf serum, 0.1 um deoxycoformycin, 10 ug/ml of penicillin and streptomycin, and in the presence and absence of 20 uM MTX. The ADA selective media (AAU) contained 1.1 mM adenosine, 10 ug/ml alanosine and 1 mM uridine. Subsequently it was shown that removal of the MTX selection at this stage resulted in a decrease in the factor VIII:c expression. Subsequently, the MTX has been left in the ADA selective media.

It was possible to amplify the VWF gene by selection for growth in increasing concentrations of 2'-deoxycoformycin (dCF) in the presence of cytotoxic concentrations of adenosine. A pool (3-a) of transformants (6 colonies) was prepared from 10A1 cells and selected for ADA in the presence of 20 uM MTX. The ADA selection mean was changed by sequentially increasing the concentration of 2'deoxycoformycin (steps of 0.1 uM, 0.5 uM, 1.0 uM and 2.0 uM) in the presence of 20 uM MTX. At each step, the production of VWF and of factor VIII:c was measured after 24 hours in the presence of 10% fetal calf serum (FCS) or in defined media. The results are summarized below:

| Coxpression of VWF and FVIII:c in CHO cell lines |||||
|---|---|---|---|---|
| | Selection || VWF Antigen || Factor VIII:c |
| Cell line | dCF uM | MTX uM | ug/ml | pg/cell | uUnits/cell |
| 10A1 (no VWF) | | | | | .38*<br>0.93** |
| 10A13a pool | 0.1 | 20 | 0.07 | 0.1 | |
| | 0.5 | 20 | 0.8 | 1.14 | 0.63*<br>0.89** |
| | 1.0 | 20 | 24 | 30 | 0.63*<br>1.1** |
| | 2.0 | 1000 | 7.4 | 24 | 1.4*<br>1.5** |

*in defined media; **in media containing 10% Fetal calf serum; VWF antigen was determined by an ELISA assay using affinity-purified rabbit-anti-VWF antiserum (Calbiochem-Behring, 782301), purified VWF antigen from normal human plasma pools to serve as standards and controls, and IgG isolated from Calbiochem-Behring, 782301, and conjugated with alkaline phosphatase. Factor VIII:c activity was determined by the chromogenic assay described in Example I.

These results demonstrate that VWF expression increased with increasing ADA selection. In addition, expression of factor VIII:c was not dependent on the presence of serum, as observed by line 10A13-a in 2 uM dCF and 1000 uM MTX which expresses 1.4 uUnits/cell/day of factor VIII:c in defined media.

EXAMPLE VIII

Fusion of CHO cells expressing Factor VIII:c and CHO cells expressing VWF

The VWF gene has been introduced into CHO DHFR deficient cells (DUKX-B11, Chasin and Urlaub, 1980, Proc. Natl. Acad. Sci. 77:44216). Two approaches have been taken in order to obtain cells that express either MTX resistance or dCF resistance associated with VWF expression. Then either cell line can be subsequently used to fuse to other cells that express factor VIII:c with the ability to select for either MTX or dCF resistance.

MTX Amplification in CHO DHFR deficient Cells

Plasmid pMT2VWF and pAdD26SVpa(3) were mixed 10:1 and transfected by CaPO4 coprecipitation into CHO DUKX-B11 cells as described by Kaufman and Sharp (1982, J. Mol. Biol. 150:601). Cells were selected for the DHFR positive phenotype by growth in the absence of nucleosides and colonies pooled and selected for increasing MTX resistance. The results indicated that VWF expression increased with increasing MTX resistance and are depicted in the Table below:

| Selection | ng/ml VWF |
|---|---|
| 0.02 uM MTX | — |

| Selection | ng/ml VWF |
|---|---|
| 0.2 uM MTX | 56 |
| 1.0 uM MTX | 91 |
| 5.0 uM MTX | 278 | dCF Selection for VWF in CHO DHFR Deficient Cells

The plasmid pMT2ADA-VWF was introduced into CHO DUKX-B11 cells as described in Example VII and cells selected for growth in ADA selective alpha media with 4 uM xyl-A, 0.03 uM dCF, 10 ug/ml hypoxanthine, 10 ug/ml thymidine, and 10 ug/ml of penicillin and streptomycin. One clone PM5F was derived which expressed 3-5 pg of VWF/cell/day. This clone was subsequently used for fusion to factor VIII:c cell lines and as a recipient for the introduction of factor VIII:c genes.

Fusion of Factor VIII:c-type and VWF Expressing Cel Lines

The factor VIII:c-type expression plasmid pLA2 has been described (pLA2 contains a transcription unit for a procoagulant B-domain 880 amino acid deletion mutant of FVIII:c, see International Application No. PCT/US86/00774). This plasmid has been introduced into DUKX-B11 CHO cells by protoplast fusion with selection for DHFR from the 3' region of the factor VIII-DHFR transcript (See PCT/US86/00774). A cell line was derived by selection for MTX resistance to 1.0 uM MTX and has been named LA3-5. This cell line expresses a deleted form of Factor VIII:c at 3-5 uUnits/cell/day (in 10% fetal calf serum). This modified factor VIII:c also binds to and requires VWF for efficient synthesis. LA3-5 was fused to PM5F and hybrids were selected that expressed both the MTX resistance and dCF resistance phenotypes.

For fusion, PM5F was treated with diethylepyrocarbonate (DEPC, 0.03% for 30 minutes on ice) in order to kill the PM5F. These cells were then fused by polyethylene glycol-induced cell fusion to LA3-5: DEPC treated PM5F cells were centrifuged onto LA 3-5 ($1.5 \times 10^6$ cells) at 2000 rpm for 8 minutes in an IEC model K centrifuge. After centrifugation, supernatant was removed and 2 ml of 50% PEG solution was added. PEG was left on for 45 seconds and cells were washed thoroughly with serum free medium. Cells were left plated with medium containing serum for 48 hrs. and were then subcultured into selective medium containing 4 uM xyl-A, 0.03 uM dCF, in the presence of 10 ug/ml of each of the following: thymidine, hypoxanthinine, streptomycin, and penicillin. However, it was not necessary to include the thymidine and hypoxanthine. A pool of hybrids was obtained which expressed 0.73 pg/cell/day of VWF and 0.2—2.0 units/ml/day of the factor VIII:c-type protein. The pool was subsequently grown in the absence of thymidine and hypoxanthine in the presence of 0.5 uM MTX. These cells were cloned in alpha media with 4 uM xyl-A, 0.03 uM dCF, and 0.5 uM MTX to obtain the following clones:

| Coexpression in CHO Cells of VWF and a Factor VIII:c-type Protein | | |
|---|---|---|
| Clone | VWF Expression (pg/cell) | Factor VIII:c-type Expression (uUnits/Cell-media) |
| E6 | 16 | 2.8 - defined |
|  |  | 3.8 - 10% FCS |
| B9 | 20 | 4.5 - defined |
|  |  | 5.1 - 10% FCS |
| H6 | 34 | 7.7 - defined |
|  |  | 8.7 - 10% FCS |
| G12 | 8. | 10.5 defined |
|  |  | 11.8 10% FCS |

These results demonstrate the ability of the cell lines coexpressing VWF and the Factor VIII:c-type protein to produce high levels of the Factor VIII:c-type protein in defined media.

EXAMPLE IX

Introduction of Factor VIII:c-type Genes into Cells Expressing VWF

A factor VIII:c deletion mutant of 907 amino acids has been constructed by heteroduplex mutagenesis (PCT/US86/00774) which directly fuses the 90 kDa cleavage site (at residue 740) to the 76 kDa cleavage site (at 1647). The resultant plasmid p90-76R has the appropriate Factor VIII:c-type transcription unit in pMT2. Protoplasts of E. coli HB101 harboring this plasmid were prepared and fused to the VWF expressing cell line PM5F as described in Example VIII. 48 hrs after recovery from protoplast fusion, the cells were subcultured into DHFR selection media (alpha media lacking nucleosides with 10% dialyzed fetal calf serum, 4 uM xyl-A, and 0.03 uM dCF. After two weeks, transformants were isolated and assayed for Factor VIII:c expression. Approximately 20% of the transformants which had arisen expressed both VWF and the Factor VIII:c deletion mutant. Results for one transformant are indicated below:

| Cell Line | Factor VIII:c Activity | Media |
|---|---|---|
| F1 | 1.5 uUnits/cell (1375 mUnits/ml) | def. media |
|  | 0.95 uUnits/cell (1330 mUnits/ml) | 10% FCS |

(with VWF = 1.69 ug/ml, 1.85 pg/cell)

These results demonstrate the ability to select for the DHFR phenotype in the PM5F cell line and to coexpress a factor VIII:c-type protein and VWF in order to alleviate the serum dependence for factor VIII:c expression.

EXAMPLE X

Accumulation of Factor VIII:c-type Proteins in the presence and absence of VWF coexpression The accumulation of Factor VIII:c-type proteins over 3 days was determined by rinsing Factor VIII:c-type expressing cells and then adding back media containing 10% fetal calf serum (FCS) or defined media containing insulin, transferin, selenium, bovine serum albumin (5 g/l) as above in Example III. Factor VIII:c assays were then conducted 24, 48 and 72 hrs later. Results are shown below for four cell lines. The Chinese hamster Factor VIII:c expressing cell line 10A1 was described in Example VII. C6 is a subclone of the 10A13a pool which coexpresses human recombinant VWF and is selected in 1 mM MTX and 2.0 uM dCF from Example VII. The LA3-5 clone and the VWF coexpressing cell line G12 express a deleted form of Factor VIII:c and have been described in Example VIII. These results demonstrate the ability of the coexpressing cell lines to accumulate very high levels of Factor VIII:c-type proteins in either serum-containing or defined media compared to the original cell lines.

| Cell Line | Media | mUnits/ml | | | Factor VIII Activity Total uUnits/cell |
|---|---|---|---|---|---|
| | | 24 hr | 48 hr | 72 hr | |
| | | Wild-type Factor VIII:c: | | | |
| 10A1 | FCS | 736 | 558 | 414 | 0.3 |
| | defined | 309 | 117 | 70 | 0.06 |
| C6 | FCS | 796 | 2976 | 5170 | 5.9 |
| | defined | 531 | 1928 | 2980 | 3.2 |
| | | Deleted Factor VIII: | | | |
| LA3-5 | FCS | 1198 | 596 | 374 | 0.5 |
| | defined | 341 | 128 | 163 | 0.2 |
| G12 | FCS | 3527 | 5420 | 6380 | 22.0 |
| | defined | 3018 | 4400 | 4110 | 13.0 |

EXAMPLE XI

Similar if not improved results relative to those obtained in the preceding examples involving use of recombinant VWF should be obtained by those practicing this invention by substituting a VWF-type protein for the recombinant wild-type VWF. This may be readily accomplished by repeating the procedures using an expression vector directing the synthesis of a desired VWF-type protein instead of the wild-type VWF. Such vectors may be produced by any of the numerous procedures known in the art, or perhaps more conveniently, by conducting oligonucleotide-directed mutagenesis as desired upon the wt VWF-encoding vectors disclosed above.

What is claimed is:

1. A process for producing high levels of recombinant factor VIII:c protein or its analogs which comprises the steps of:
   (a) adding a serum-free preparation of phospholipid to a serum-free culture medium containing mammalian cells transfected with an expression vector containing DNA encoding recombinant factor VIII:c protein or its analogs, said phospholipid being added in an amount greater than 100 ug/ml of culture medium,
   (b) culturing said cells in said medium under suitable culture conditions to produce said factor VIII:c or its analogs, and
   (c) recovering said factor VIII:c or its analogs from said medium.

2. The process according to claim 1 wherein the DNA encodes human Factor VIII:c.

3. The process according to claim 1 wherein the mammalian cells are CHO cells.

4. The process according to claim 2 wherein the mammalian cells are CHO cells.

* * * * *